(12) United States Patent
Loganathan

(10) Patent No.: US 9,320,630 B2
(45) Date of Patent: Apr. 26, 2016

(54) IMPLANT DELIVERY ASSEMBLY AND METHOD OF USE

(71) Applicants: STRYKER CORPORATION, Kalamazoo, MI (US); STRYKER NV OPERATIONS LIMITED, Dublin (IE)

(72) Inventor: Siddharth Loganathan, Santa Clara, CA (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 145 days.

(21) Appl. No.: 14/100,537

(22) Filed: Dec. 9, 2013

(65) Prior Publication Data

US 2014/0180383 A1 Jun. 26, 2014

Related U.S. Application Data

(60) Provisional application No. 61/745,936, filed on Dec. 26, 2012.

(51) Int. Cl.
*A61F 2/06* (2013.01)
*A61F 2/95* (2013.01)
*A61F 2/966* (2013.01)
*A61F 2/962* (2013.01)

(52) U.S. Cl.
CPC . *A61F 2/95* (2013.01); *A61F 2/962* (2013.01); *A61F 2002/9505* (2013.01); *A61F 2002/9665* (2013.01)

(58) Field of Classification Search
None
See application file for complete search history.

(56) References Cited

U.S. PATENT DOCUMENTS

| 6,254,608 | B1 | 7/2001 | Solar |
| 6,413,269 | B1 | 7/2002 | Bui et al. |
| 6,589,274 | B2 | 7/2003 | Stiger et al. |
| 7,037,330 | B1 | 5/2006 | Rivelli, Jr. et al. |
| 7,794,488 | B2 | 9/2010 | Vrba et al. |
| 2007/0250151 | A1* | 10/2007 | Pereira ........................ 623/1.12 |
| 2011/0257720 | A1* | 10/2011 | Peterson et al. ............. 623/1.11 |

* cited by examiner

*Primary Examiner* — Robert Lynch
(74) *Attorney, Agent, or Firm* — Vista IP Law Group LLP

(57) ABSTRACT

A medical assembly for delivering an implant comprising a tubular resilient implant defining an inner lumen, the implant comprising a plurality of engaging members extending proximally an end thereof, the implant having a delivery configuration, and a released configuration, and a delivery assembly for delivering the implant, the delivery assembly comprising an outer tubular member extending through the inner lumen of the implant, the outer tubular member having a plurality of slots receiving therethrough the engaging members, with the implant being disposed in its delivery configuration on an outer surface of the outer tubular member, an inner tubular member coaxially disposed within the outer tubular member and movable relative to the outer tubular member, the inner tubular member having a first axial position that restrains the engaging members, and a second axial position to thereby release the implant from the delivery assembly.

20 Claims, 14 Drawing Sheets

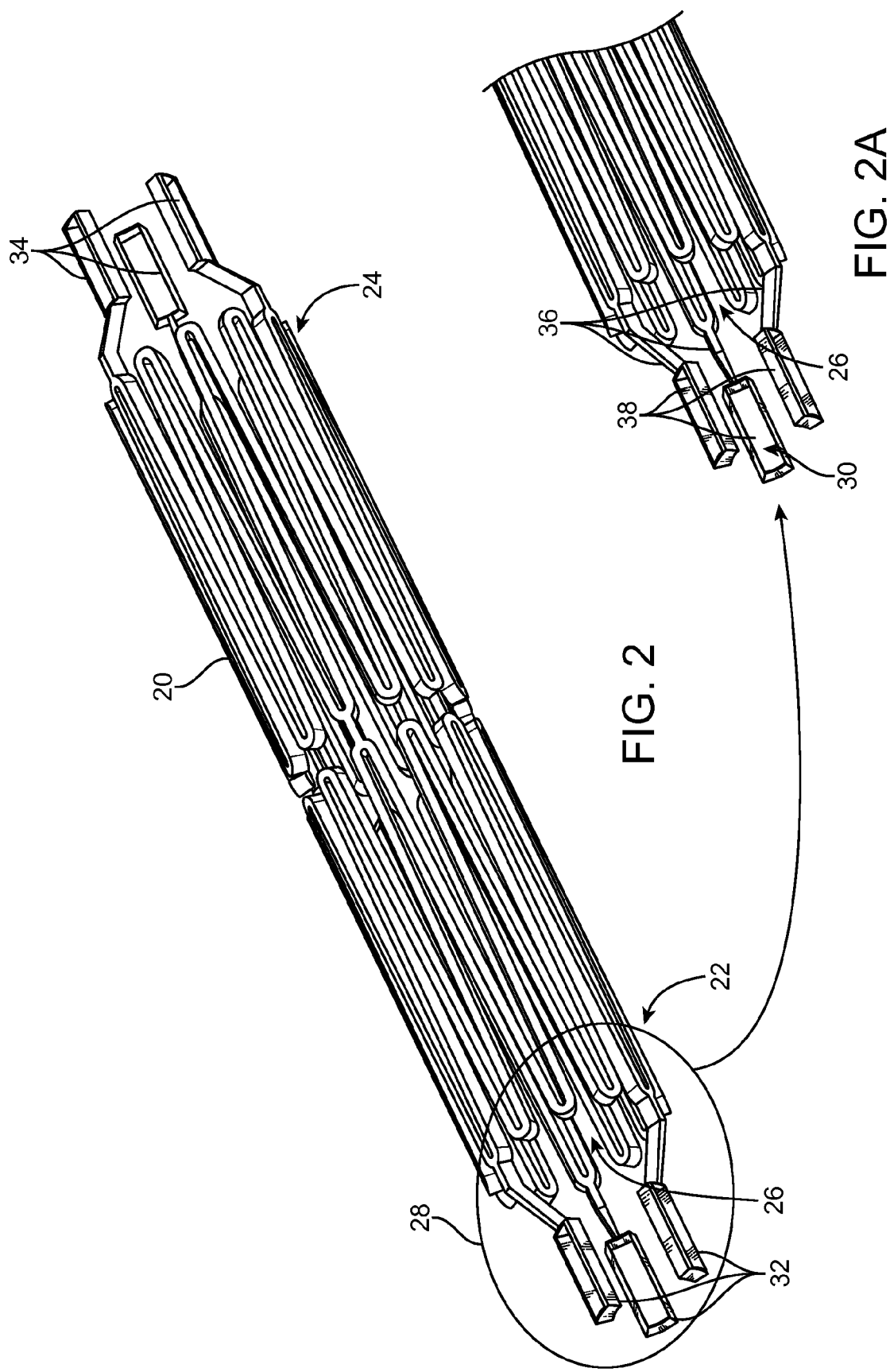

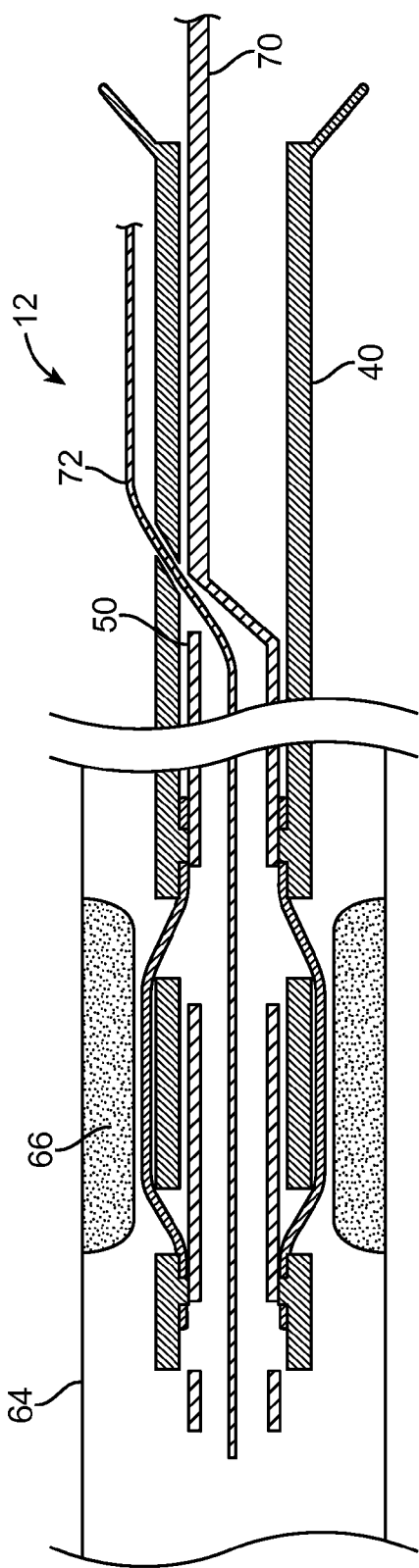
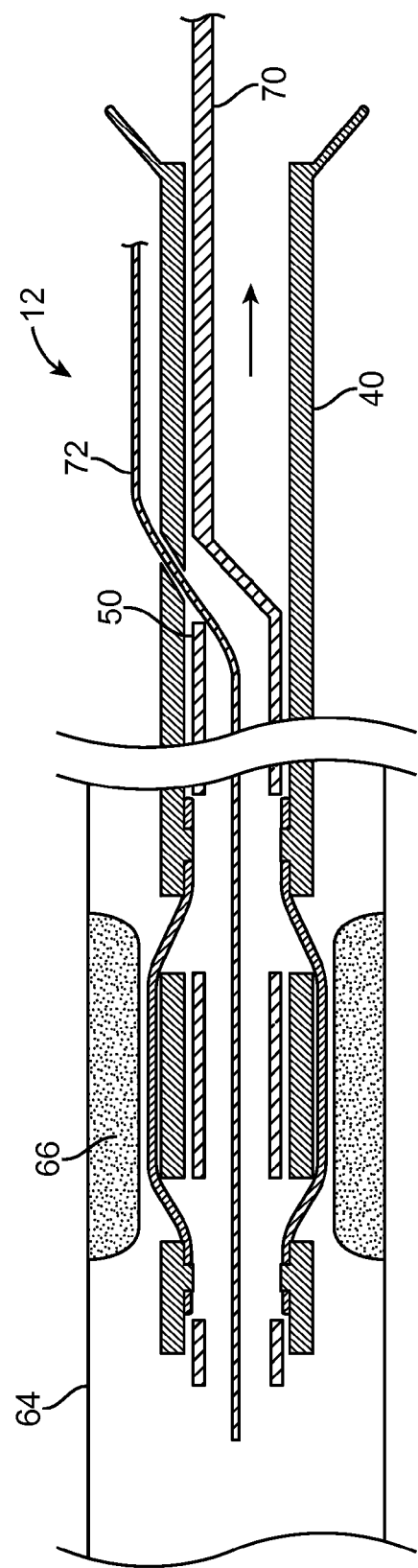
FIG. 7A
FIG. 7B

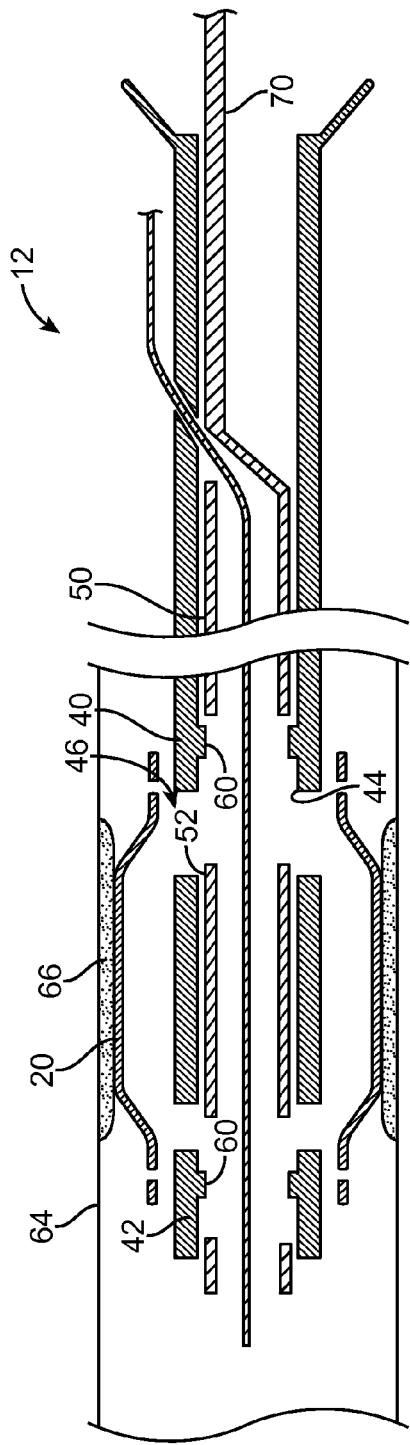
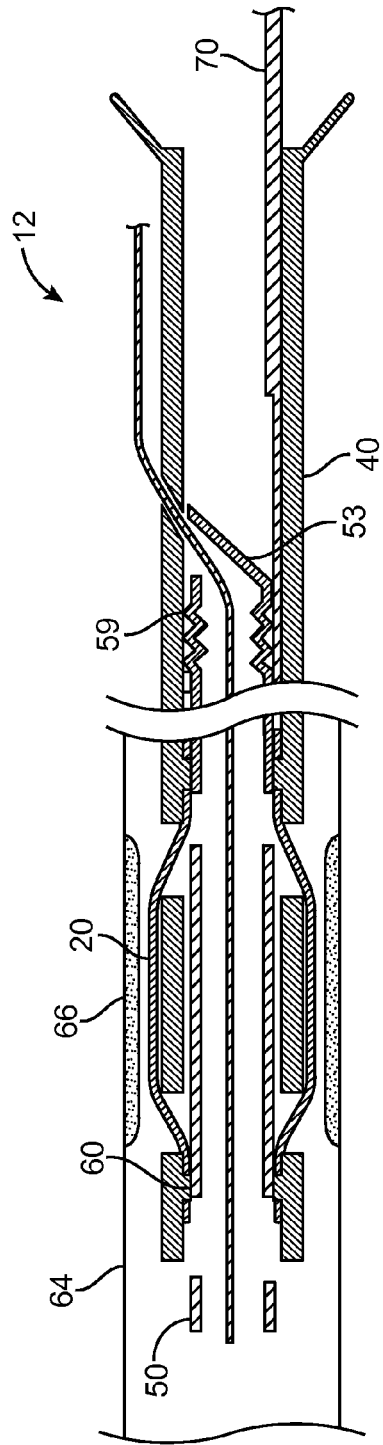
FIG. 7C
FIG. 8

IMPLANT DELIVERY ASSEMBLY AND METHOD OF USE

RELATED APPLICATION DATA

The present application claims the benefit under 35 U.S.C. §119 to U.S. provisional patent application Ser. No. 61/745,936, filed Dec. 26, 2012. The foregoing application is hereby incorporated by reference into the present application in its entirety.

FIELD OF THE INVENTION

The present disclosure relates generally to medical assemblies for delivering implants. More particularly, the present disclosure relates to delivery assemblies for delivering stents to a target site in a vasculature of a patient.

BACKGROUND

The use of intravascular medical devices and implants has become an effective method for treating many types of vascular disease. In general, a suitable intravascular device is inserted into the vascular system of the patient and navigated through the vasculature to a target site in a patient. Using this method, virtually any target site in the patient's vascular system may be accessed, including the coronary, cerebral, and peripheral vasculature.

Catheters are often utilized to place medical implants, such as stents and embolic devices, at a desired location within the body. A medical implant may be loaded onto a catheter in a configuration having a reduced diameter and then introduced into the lumen of a body vessel. For example, self-expanding stents are to be delivered in an elastically compressed state while being confined within a tubular restraining member, and then allowed to elastically expand into engagement with the interior of the body vessel when removed from the tubular restraining member. Once delivered to a target location within the body, the expanded and enlarged stent configuration supports and reinforces the vessel wall while maintaining the vessel in an open and unobstructed condition.

Various types of delivery systems are used in a number of intravascular applications for delivering self-expanding stents, such as the so-called "over-the-wire" and "rapid-exchanged" delivery systems. In the "over-the-wire" delivery system, a catheter is introduced into the patient over a guidewire which has been previously introduced; the guidewire extends through the entire length of the catheter through a lumen of the catheter. In the "rapid-exchange" delivery system, the guidewire extends through only a distal portion of the catheter from the distal tip to a guidewire port located proximal of the distal tip. In the "over-the-wire" and "rapid-exchanged" delivery systems, stents are loaded and confined within the inner wall of a catheter narrowing the lumen defined by the inner wall of the catheter and reducing its flushing capabilities. Further, stents confined within the inner wall of the delivery catheters are coaxially disposed over the guidewire, which alters the guidewire position during delivery of a stent.

Therefore, there is an ongoing need to provide an implant delivery system for delivering a self-expanding stent that facilitates flushing capabilities and minimize alteration of the guidewire position during stent deployment.

SUMMARY

In one embodiment of the disclosed inventions, a medical assembly for delivering an implant into a target site of a patient, the assembly comprises a tubular resilient implant having a proximal end, a distal end, and defining an inner lumen extending therebetween. The implant comprises a first plurality of engaging members extending proximally from the proximal end, and a second plurality of engaging members extending distally from the distal end, wherein the respective engaging members of the first and second plurality of engaging members are biased to extend radially inward or otherwise elastically deformed. The implant having a delivery configuration in which the implant is radially constrained, and a released configuration in which the implant is radially expanded. The medical assembly comprising a delivery assembly for delivering the implant. The delivery assembly comprising an outer tubular member extending through the inner lumen of the implant, the outer tubular member having a first plurality of slots receiving therethrough the first plurality of engaging members, and a second plurality of slots receiving therethrough the second plurality of engaging members, respectively, with the implant being disposed in its delivery configuration on an outer surface of the outer tubular member. The delivery assembly comprises an inner tubular member coaxially disposed within the outer tubular member and movable relative to the outer tubular member. The inner tubular member having a first axial position in which the inner tubular member restrains the respective first and second pluralities of engaging members between an outer surface of the inner tubular member and an inner surface of the outer tubular member, and a second axial position in which the resiliency of the implant causes the first and second plurality of engaging members to withdraw out of the respective first and second plurality of slots, thereby releasing the implant from the delivery assembly.

By way of non-limiting examples, the engaging members of the first and second pluralities of engaging members may have paddle-like configurations, each engaging member including a first portion that extends from the implant through a respective slot in the outer tubular member. The engaging member further comprises a second portion that engages a respective protrusion extending radially inward from the inner surface of the outer tubular member or extending radially outward from the outer surface of the inner tubular member. By way of example, the protrusions may extend radially inward from the inner surface of the outer tubular member or radially outward from the outer surface of the inner tubular member. The second portion of each engaging member comprises a loop-like, a hook-like or a C-like configuration.

In such embodiments, the inner tubular member comprises a first plurality of openings therein and a second plurality of openings therein, where the first and second plurality of openings are sized to release the respective first and second plurality of engaging members from the protrusions and out of the respective first and second plurality of slots when the inner tubular member is moved from the first axial position to the second axial position.

In another embodiment of the disclosed inventions, a medical assembly for delivering an implant into a target site of a patient comprises a tubular resilient implant defining an inner lumen extending therebetween. The implant comprising a plurality of engaging members extending from an end thereof, wherein the engaging members are biased to extend radially inward or otherwise elastically deformed. The implant having a delivery configuration in which the implant is radially constrained, and a released configuration in which the implant is radially expanded. The medical assembly further comprises a delivery assembly for delivering the implant; the delivery assembly comprises an outer tubular member extending through the inner lumen of the implant. The outer tubular member having a plurality of slots receiving therethrough the engaging members, with the implant being disposed in its delivery configuration on an outer surface of the outer tubular member. The delivery assembly comprises an inner tubular member coaxially disposed within the outer tubular member and movable relative to the outer tubular member. The inner tubular member having a first axial position in which the inner tubular member restrains the engaging members between an outer surface of the inner tubular member and an inner surface of the outer tubular member, and a second axial position in which the resiliency of the implant causes the engaging members to withdraw out of the slots, thereby releasing the implant from the delivery assembly.

By way of non-limiting examples, the engaging members have paddle-like configurations, each engaging member including a first portion that extends from the implant through a respective slot in the outer tubular member. Each engaging member further comprises a second portion that engages a respective protrusion of the delivery assembly. By way of example, the protrusions extend radially inward from the inner surface of the outer tubular member and/or the protrusions extend radially outward from the outer surface of the inner tubular member. The second portion of each engaging member comprises a loop-like, a hook-like or a C-like configuration.

In some embodiments, the inner tubular member comprises a plurality of openings sized to release the engaging members from the protrusions and out of the slots when the inner tubular member is moved from the first axial position to the second axial position.

In some embodiment, the implant is made out of a compressible, elastic material and/or the implant is a stent.

In some embodiments, the delivery assembly comprises a detachment member secured to a proximal portion of the inner tubular member for moving the inner tubular member from the first axial position to the second axial position.

In other embodiments, the medical assembly comprises a guidewire having a distal end portion slidable disposed within the inner tubular member.

Other and further aspects and features of embodiments of the disclosed inventions will become apparent from the ensuing detailed description in view of the accompanying figures.

BRIEF DESCRIPTION OF THE DRAWINGS

FIGS. 7A-C are cross-sectional views of an exemplary method of delivering an implant into a target site of a patient using the implant delivery assembly of FIG. 1;

FIG. 8 is cross-sectional views of some embodiments of the disclosed inventions.

DETAILED DESCRIPTION OF THE ILLUSTRATED EMBODIMENTS

Figure 1:
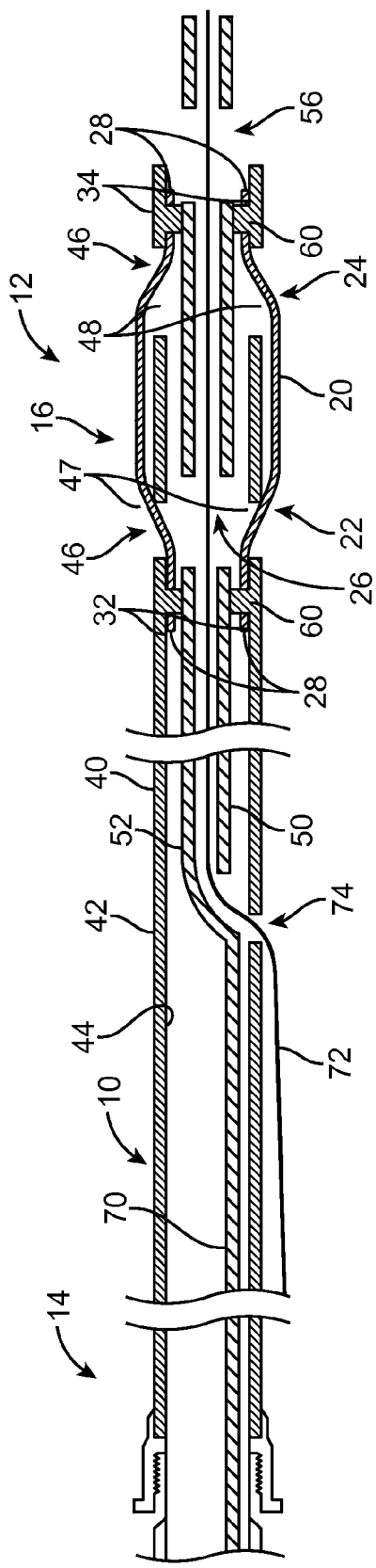
FIG. 1 is a cross-sectional view of an implant delivery assembly constructed according to one embodiment of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 1 is a cross-sectional view of a medical assembly 10 for delivering an implant 20 into a target site of a patient, constructed in accordance with a one embodiment of the disclosed inventions. The medical assembly 10 includes an implant 20, such a stent, and a delivery assembly 12 to which the implant 20 is detachably coupled. The delivery assembly 12 and implant 20 may be composed of suitable polymeric material. The delivery assembly 12 is dimensioned to reach remote locations of a vasculature and is configured to deliver the implant 20 to a target location, such as an occlusion in a blood vessel. The delivery assembly 12 includes a tubular member interface having an outer tubular member 40 and an inner tubular member 50 coaxially disposed within the outer tubular member 40 and movable relative to the outer tubular member 40 to release the implant 20 from the delivery assembly 12.

The implant 20 includes a tubular resilient configuration having a proximal end 22, a distal end 24, and defining an inner lumen 26 extending therebetween. The implant 20 further includes a plurality of engaging members 28 that extend from the proximal end 22 and the distal end 24, respectively. Particularly, the implant 20 includes a first plurality of engaging members 32 extending proximally from the proximal end 22, and a second plurality of engaging members 34 extending distally from the distal end 24. The respective engaging members of the first 32 and second 34 plurality of engaging members are biased to extend radially inward towards the inner lumen 26 of the implant 20. Alternatively, the engaging members of the first 32 and second 34 plurality of engaging members are elastically deformed to engage the delivery assembly 12 interface.

Further, the implant 20 is disposed on the outer tubular member 40 of the delivery assembly 12. The outer tubular member 40 includes an outer surface 42, an inner surface 44 and a plurality of slots 46. The slots 46 are located at a distal portion 16 of the delivery assembly 12, and include a first plurality of slots 47 configured to receive the first plurality of engaging members 32, and a second plurality of slots 48 configured to receive the second the plurality of engaging members 34, respectively, when the implant 20 is disposed on the outer surface 42 of the outer tubular member 40.

Within the outer tubular member 40, an inner tubular member 50 is coaxially disposed and axially movable relative to the outer tubular member 40. The inner tubular member 50 movements include a first axial position in which the inner tubular member 50 restrains the respective first 32 and second 34 pluralities of engaging members between an outer surface 52 of the inner tubular member 50 and the inner surface 44 of the outer tubular member 40 holding the implant 20 with the delivery assembly. The inner tubular member 50 movements further include a second axial position in which the resiliency of the implant 20 causes the first 32 and second 34 plurality of engaging members to withdraw out of the respective first 47 and second 48 plurality of slots, thereby releasing the implant 20 from the delivery assembly 12 (shown in FIGS. 7B-C). The inner tubular member 50 movements include a range of axial motion between the first axial position and the second axial position. It will be appreciated that the range of movement of the inner tubular member 50 between first and second axial positions provides a controlled release in stages of the respective first 32 and second 34 plurality of engaging members. For example, depending on the location of the slots 46 and/or openings 56 of the delivery assembly 12, either the first plurality of engaging members 32 may be released from the delivery assembly 12 before the second plurality of engaging members 34 are released, or the first plurality of engaging members 32 may be released from the delivery assembly 12 after the second plurality of engaging members 34 are released.

Within the inner tubular member 50 of the delivery assembly 12 a guidewire 72 may be disposed. The medical assembly 10 may be used in an "over-the-wire" configuration (not-shown), wherein the delivery assembly 12 is introduced into the patient over a guidewire which has been previously introduced; and the delivery assembly 12 extends through the entire length of a medical assembly and over the entire length of the guidewire. Preferably, the medical assembly 10 may be used in a "rapid-exchange" configuration as shown in FIG. 1; the guidewire 72 extends through only the distal portion 16 of the medical assembly 10 from a guidewire port 74. The guidewire port 74 may be located intermediate the proximal portion 14 and the distal portion 16 of the medical assembly 10 providing the delivery assembly 12 with "rapid-exchange" capabilities.

The medical assembly 10 may include one or more, or a plurality of regions along its length having different configurations and/or characteristics. For example, the distal portion 16 of the medical assembly may have an outer diameter less than the outer diameter of the proximal portion 14 to reduce the profile of the distal portion 16 and facilitate navigation in tortuous vasculature. Furthermore, the distal portion 16 may be more flexible than the proximal portion 14. Generally, the proximal portion 14 may be formed from material that is stiffer than the distal portion 16 of the medical assembly 10, so that the proximal portion 14 has sufficient pushability to advance through the patient's vascular system, while the distal portion 16 may be formed of a more flexible material so that the distal portion 16 may remain flexible and track more easily over the guidewire 72 to access remote locations in tortuous regions of the vasculature. In some instances, the proximal portion 14 may include a reinforcement layer, such a braided layer or coiled layer to enhance the pushability of the medical assembly 10. The medical assembly 10 may include a transition region between the proximal portion 14 and the distal portion 16. The guidewire port 74 may be located proximal of the transition region, thus located in the proximal portion 14 of the medical assembly 10.

The delivery assembly 12 may further includes a detachment member 70 secured to a proximal portion of the inner tubular member 50 for axially moving the inner tubular member 50 from the first axial position to the second axial position. The detachment member 70 may be directly or indirectly coupled to the inner tubular member 50 or being a portion of the inner tubular member 50 proximally extending therewith. The detachment member 70 may be formed of suitable polymeric material.

Figure 2C:
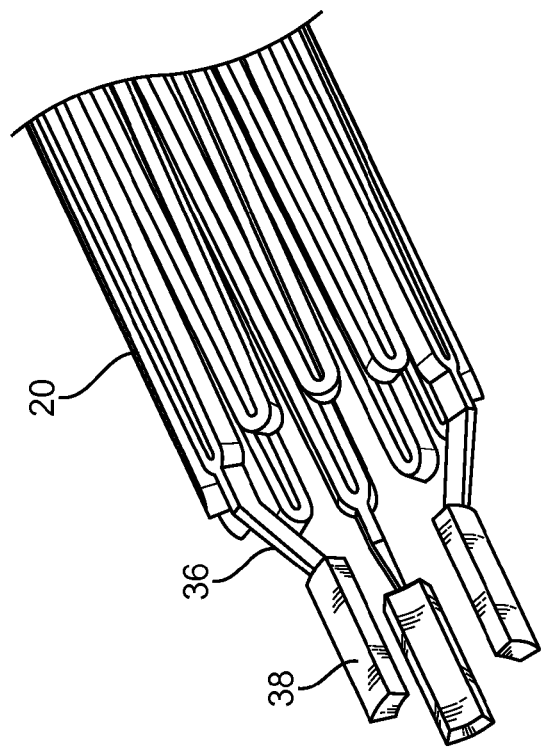
FIGS. 2-2C are a perspective view of an implant according to one embodiment of the disclosed inventions, including insets showing a plurality of engaging members of the implant and other embodiments of the engaging members in FIGS. 2A-C.
Figure 2B:
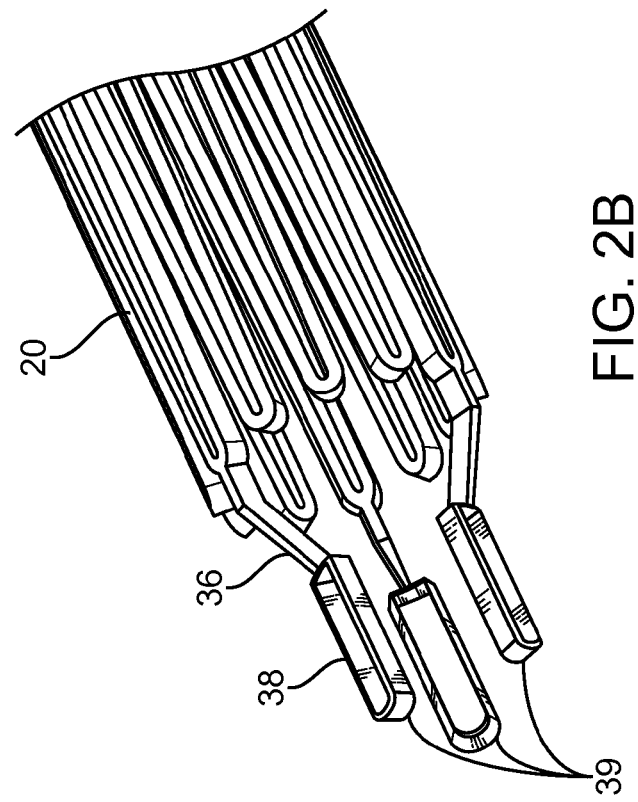

FIG. 2 illustrates the implant 20 according to the one embodiment of the disclosed inventions, including insets FIGS. 2A-C showing the plurality of engaging members 28 according to the embodiments of the disclosed inventions. The tubular resilient implant 20 has a delivery configuration in which the implant 20 is radially constrained, and a released configuration in which the implant 20 is radially expanded. The implant 20 may be formed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol. The implant 20 may be a self-expanded stent.

The first plurality of engaging member 32 extending from the proximal end 22 of the implant 20, and the second plurality of engaging member 34 extending from the distal end 24 of the implant 20 have a paddle-like configuration biased to extend radially inward towards the inner lumen 26 of the implant 20. Alternatively, the engaging members of the first 32 and second 34 plurality of engaging members are elastically deformed. Each of the engaging members 28 have a first portion 36 extending from the implant 20 and configured to be disposed through a respective slot 46 in the outer tubular member 40, and a second portion 38 extending from the first portion 36 and configured to be engaged by the delivery assembly 12, for example by the interface between the outer 40 and inner 50 tubular members and/or by a protrusion 60 (shown in FIGS. 5B-6D).

The engaging members 28 may further include a loop-like configuration where the second portion 38 loops back to the first portion 36 of each engaging member 28, such as an eye-of-a-needle configuration where the second portion 36 of each engaging member defines a hole 30 as shown in FIG. 2A. Further, the second portion 38 of each engaging members 28 may comprise a semi-rounded, non-traumatic end 39 as shown in FIG. 2B. In some instances, the second portion 38 of each engaging members 28 may be include a solid configuration without holes as shown in FIG. 2C. Alternatively, the second portion 38 may include a hook-like or C-like configuration (not shown).

Figure 3A:
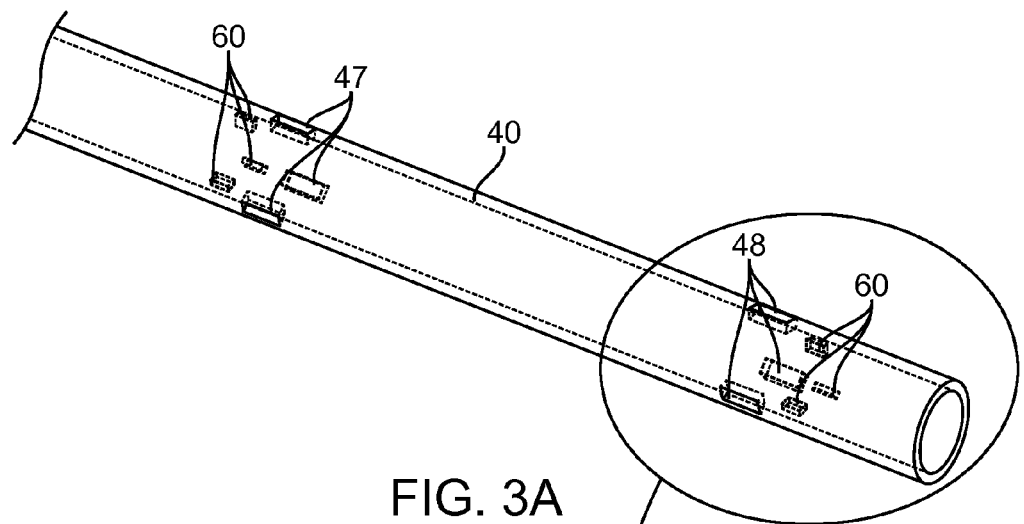
FIGS. 3A-B are perspective and cross-sectional views, respectively, of the outer tubular member of the implant delivery assembly.
Figure 3B:
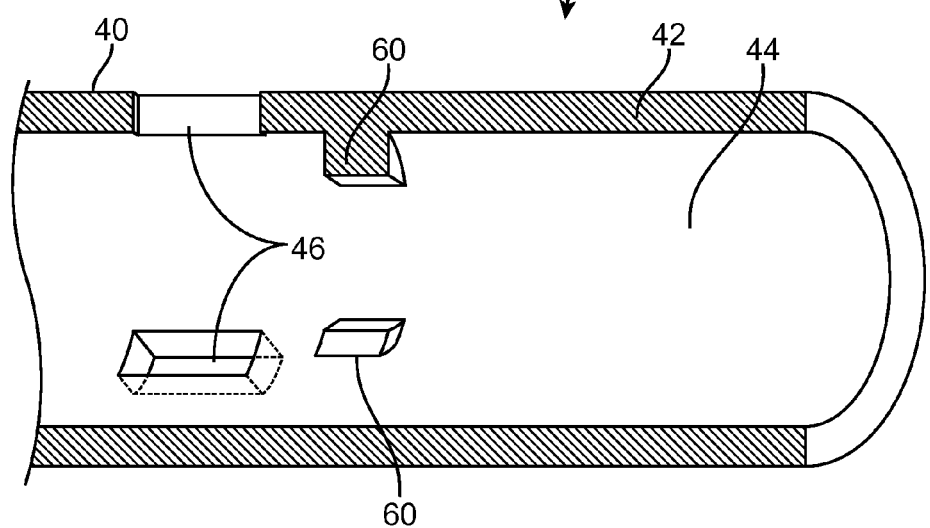
Figure 5A:
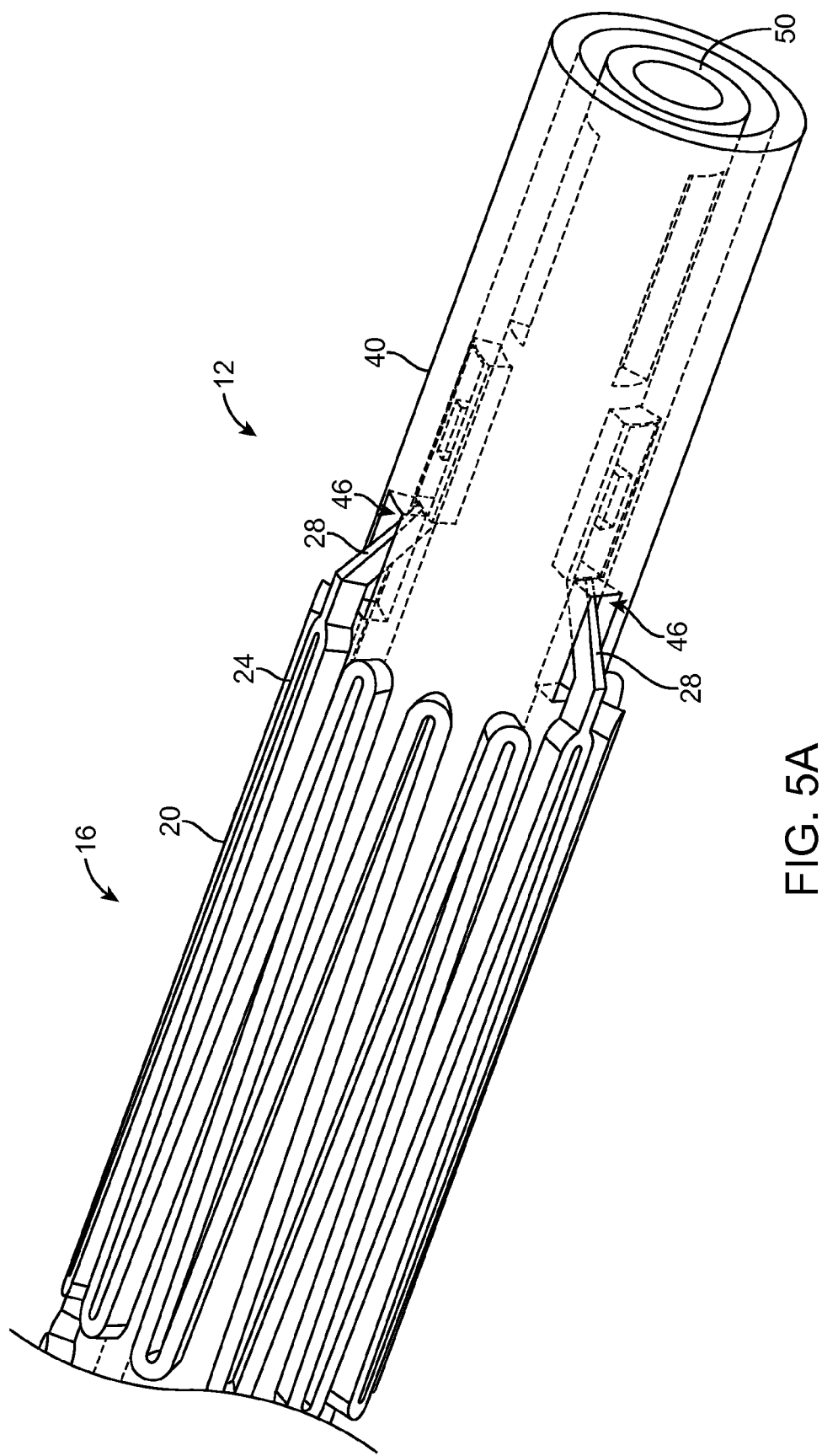
FIGS. 5A-B are perspective and cross-sectional views, respectively, of a distal portion of the implant delivery assembly of FIG. 1.
Figure 5B:
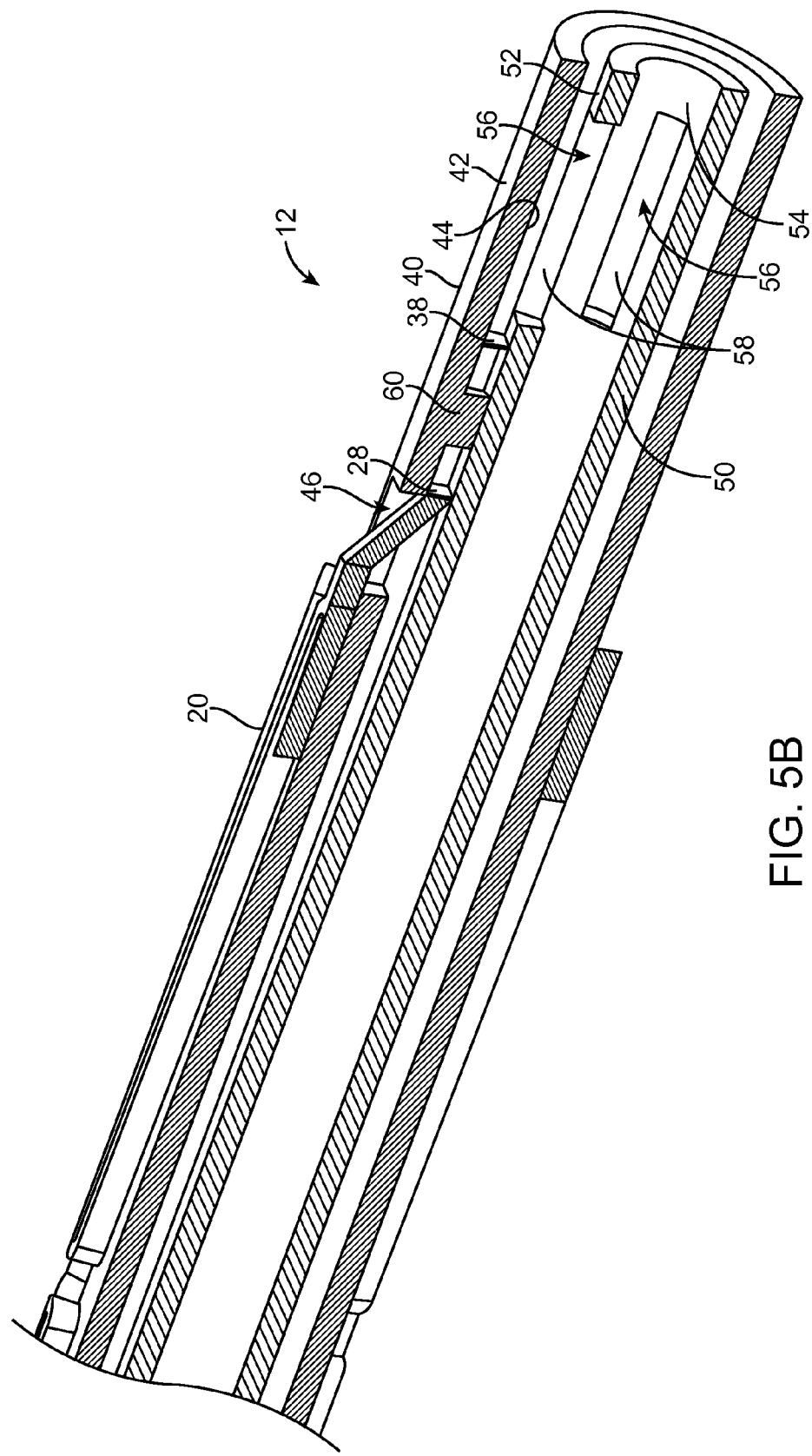

FIGS. 3A-B illustrate the outer tubular member 40 of the delivery assembly 12 according to the one embodiment of the disclosed inventions. The slots 46 of the outer tubular member 40 are sized and located to receive the plurality of engaging members 28 of the implant 20 when the outer tubular member 40 extends through the inner lumen 26 of the implant during the implant delivery configuration. The first plurality of slots 47 are configured to receive the first plurality of engaging members 32, and the second plurality of slots 48 are configured to receive the second the plurality of engaging members 34, respectively, when the implant 20 is disposed on the outer surface 42 of the outer tubular member 40 (FIGS. 5A-B).

Various arrangements and configurations of slots 46 may be contemplated. As shown, the slots 28 are disposed at the same or a similar angle with respect to the longitudinal axis of outer tubular member 40. In some embodiments, at least some, if not all of slots 46 are disposed at a different angle with respect to the longitudinal axis of outer tubular member 40 (not shown), as long as, the slots 46 are configured to receive the engaging members 28.

The outer tubular member 40 further includes protrusions 60 disposed in the inner surface 44 of the outer tubular member 40. In one embodiment, each protrusion 60 extends radially inward from the inner surface 44 of the outer tubular member 40. Further, the protrusions 60 are sized, located and configured to engage a respective engaging member 28, particularly, the second portion 38 of the engaging members 28. Those skilled in the art will appreciate that various arrangements and configurations of the protrusions 60 may be contemplated. By way of example, the protrusions 60 can have a variety of shapes including but not limited to: a circular, oval, rectangular (as shown), multi-sided, or irregular shapes, and/or angles that are adapted to mate and engage with the engaging members 28 of a corresponding or different shape and/or angle.

Figure 4A:
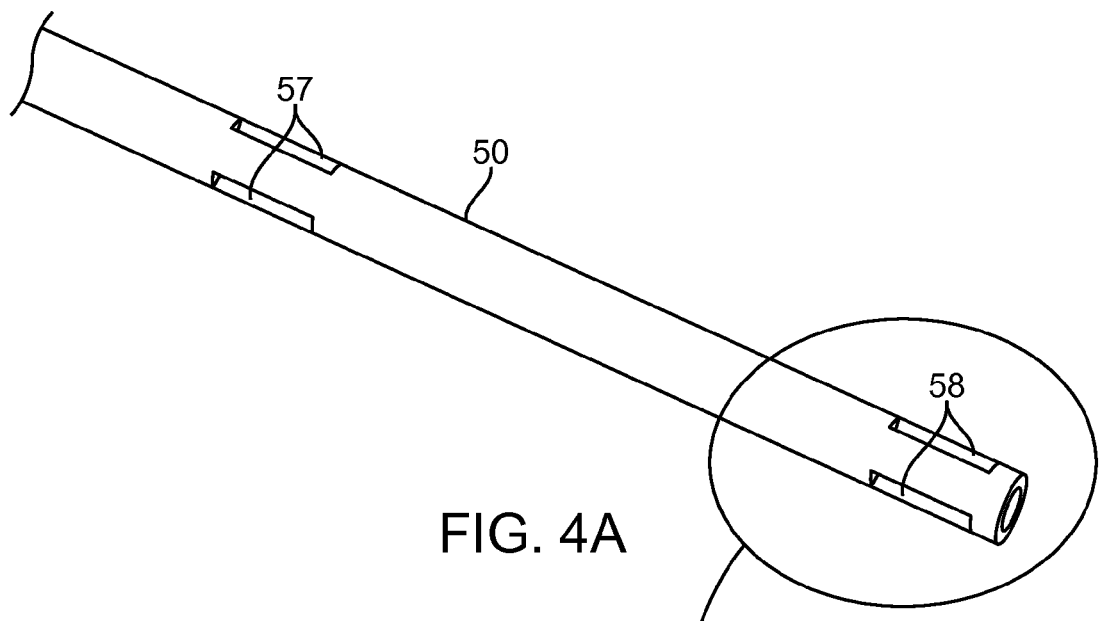
FIGS. 4A-B are perspective and cross-sectional views, respectively, of the inner tubular member of the implant delivery assembly.
Figure 4B:
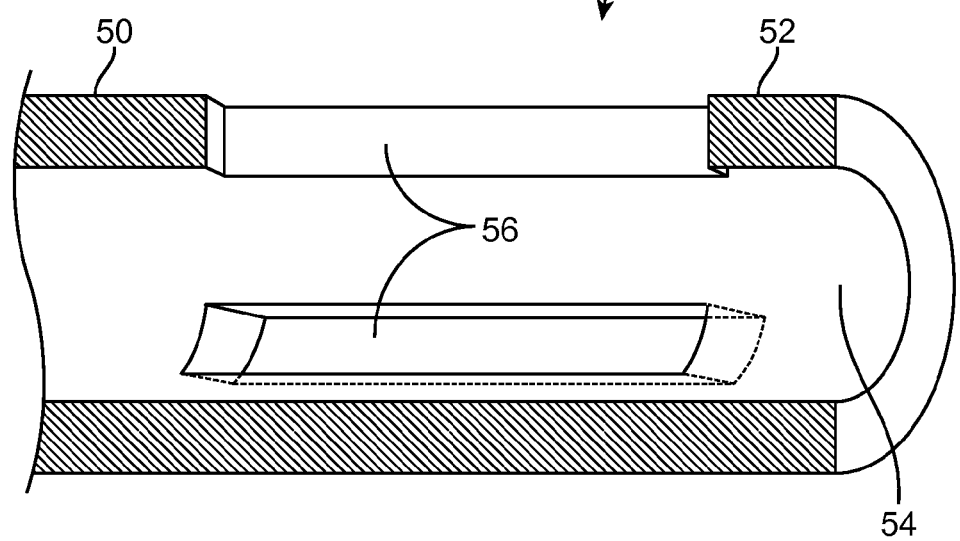

FIGS. 4A-B illustrate the inner tubular member 50 of the delivery assembly 12 according to the one embodiment of the disclosed inventions. The inner tubular member 50 comprises an outer surface 52, an inner surface 54, and a plurality of openings 56, having a first plurality of openings 57 and a second plurality of openings 58. The first 57 and second 58 plurality of openings are sized to release the respective first 32 and second 34 plurality of engaging members from the protrusions 60 and out of the respective first 47 and second 48 plurality of slots when the inner tubular 50 member is moved from the first axial position to the second axial position.

As shown in FIGS. 5A-B, the distal portion of 16 of the medical assembly 10 is illustrated according to one embodiment of the disclosed inventions. The implant 20 is positioned over the outer tubular member 40 of the delivery assembly 12, where the engaging members 28 of the implant 20 that are biased to extend radially inward, or otherwise elastically deformed, are received by the plurality of slots 46 of the outer tubular member 40. The delivery assembly 12 interface includes the outer tubular member 40 and the inner tubular member 50, the inner tubular member 50 is coaxially disposed within the outer tubular member 40 and movable relative to the outer tubular member 40 to release the implant 20 from the delivery assembly 12. While the implant 20 is in its delivery configuration, the engaging members 28 are constricted and/or held by the delivery assembly 12 interface, such as, the first axial position of the inner tubular member 50 with respect to the outer tubular member 40. Further, each engaging member 28 received by a respective slot 46 is engaged by a respective protrusion 60 that extends radially inward from the inner surface 44 of the outer tubular member 40, as shown in FIG. 5B. The inner tubular member openings 56 are sized to release the respective engaging members 28 from the protrusions 60 and out of the respective slots 46 when the inner tubular 50 member is moved from the first axial position to the second axial position.

Figure 6A:
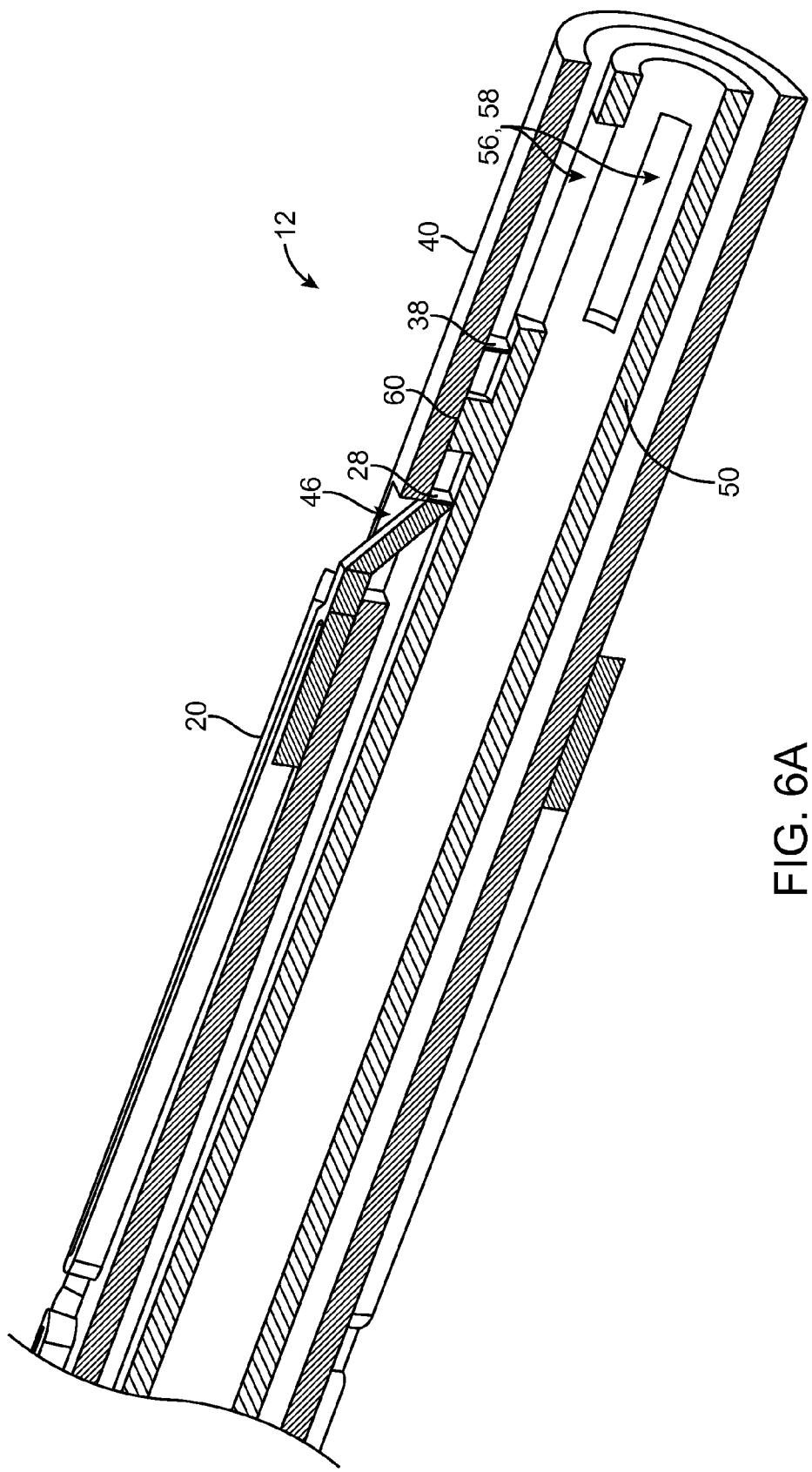
FIGS. 6A-D are cross-sectional views of some embodiments of the distal portion of the implant delivery assembly of FIG. 1.
Figure 6B:
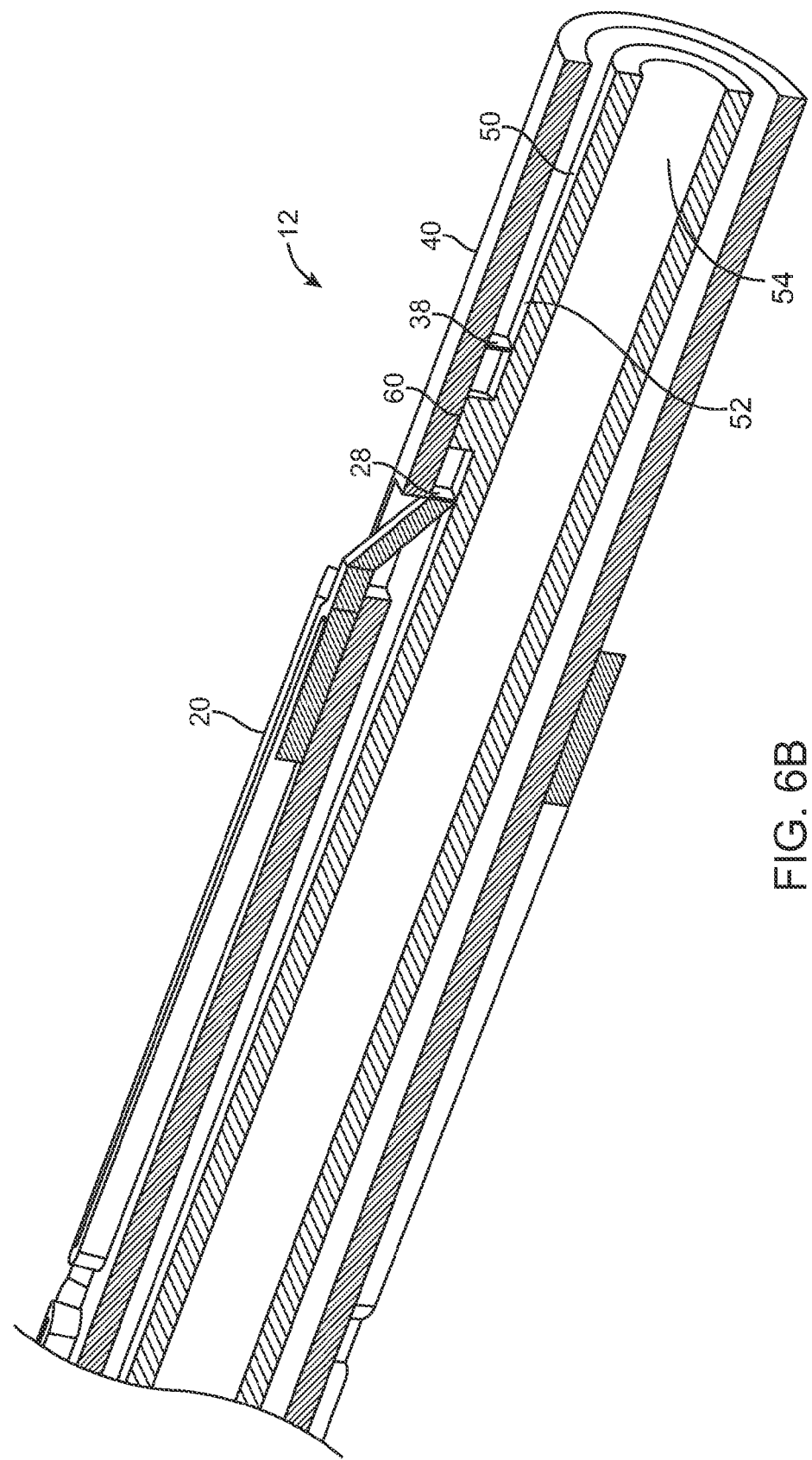

In another embodiment of the delivery assembly 12, the protrusions 60 extend radially outward from the outer surface 52 of the inner tubular member 50, as shown in FIGS. 6A-B. Unlike the embodiment of FIGS. 5A-B, in the embodiment of FIG. 6B is not necessary for the inner tubular member 50 to have a second plurality of openings 58. Those skilled in the art will recognize that at least some of the protrusions 60 may extend radially inward from the inner surface 44 of the outer tubular member 40 and some other protrusions 60 may extend radially outward from the outer surface 52 of the inner tubular member 50 in the delivery assembly 12 (not shown). These alternative configuration are recognized as long as the location of the respective slots 46 in the outer tubular member 40 and the respective openings 56 in the inner tubular member 50 allow the engaging members 28 to be released and the implant 20 to be delivered when the inner tubular member 50 moves from the first axial position to the second axial position.

Figure 6C:
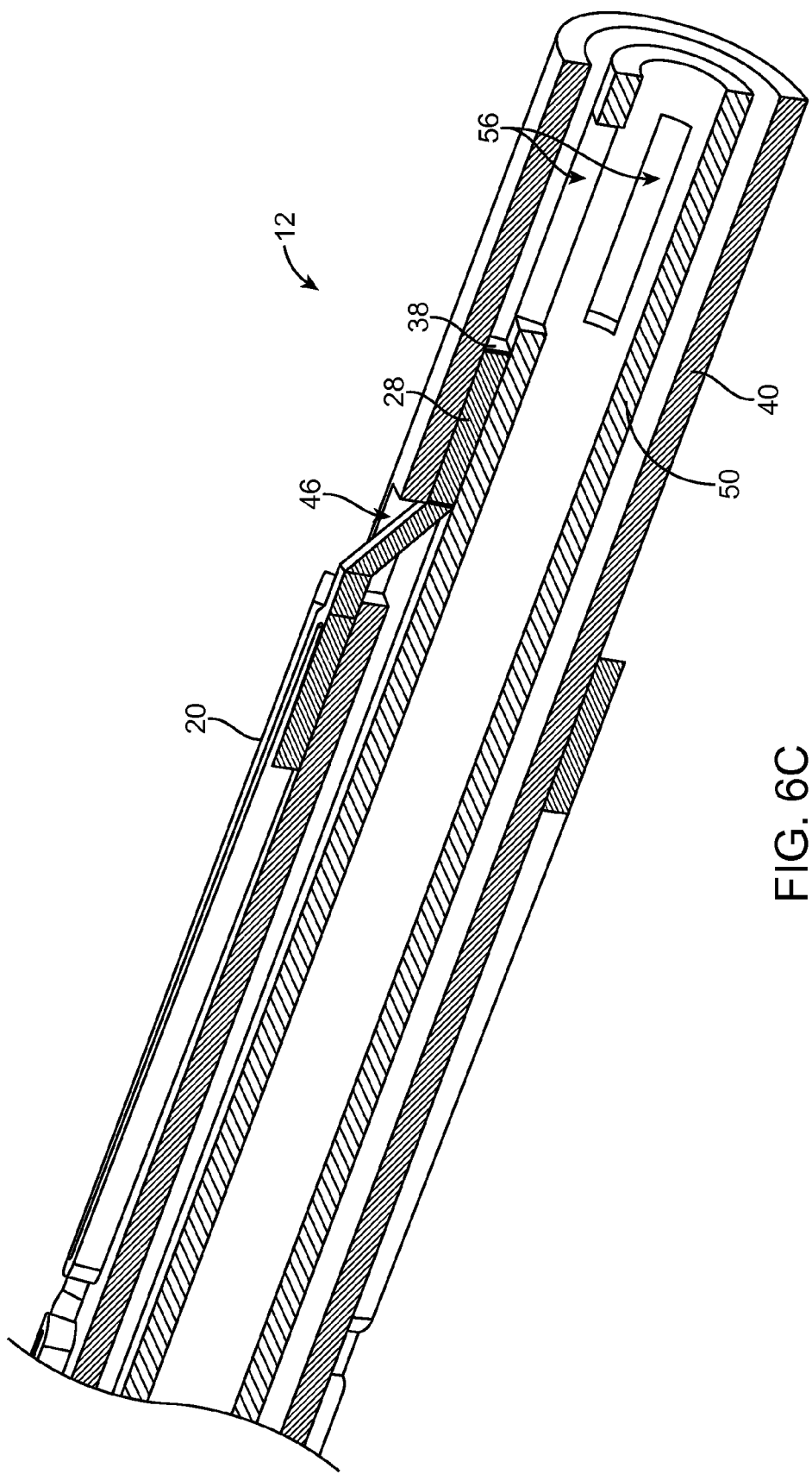
Figure 6D:
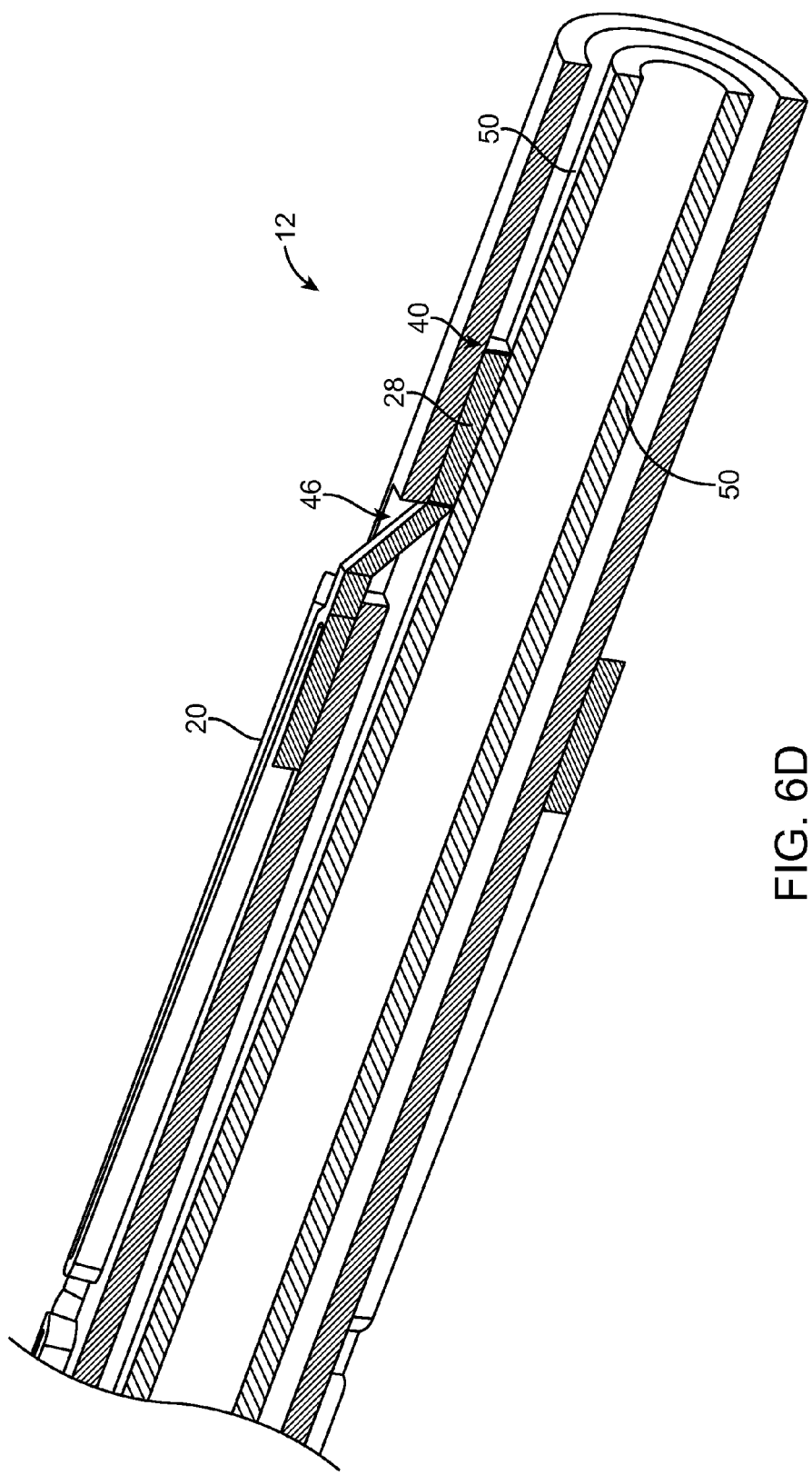

FIGS. 6C-D illustrates others embodiments of the delivery assembly 12 where the engaging members 28 of the implant 20 have the second portions 38 shown in FIG. 2C. In the embodiment of FIGS. 6C-D, slots 46 are not necessary, and in the embodiment of FIG. 6D, the plurality of openings 56 are not necessary.

FIGS. 7A-C illustrate an exemplary method of delivering the implant 20 to an occlusion 66 of a blood vessel 64 using the medical assembly 10 of FIG. 1. After gaining access to the vasculature of the patient, the guidewire 72 may be advanced through the blood vessel 64 to a location proximate to the occlusion 66 to establish a pathway along which the delivery assembly 12 having implant 20 may be advanced via the guidewire 72. After the guidewire 72 has been positioned in a desired location, the delivery assembly 12 may be advanced over the guidewire 72. Once the delivery assembly 12 has been advanced to the treatment site and the implant 20 is at the desired target site proximate the occlusion 66, the inner tubular member 50 of the delivery assembly 12 is axially moved relative to the outer tubular member 40 to thereby release the implant 20 from the delivery assembly 12. The inner tubular member 40 is moved from the first axial position in which the inner tubular member 40 restrains the engaging members 28 between the outer surface of the inner tubular member 52 and an inner surface of the outer tubular member 44 (FIG. 7A), to the second axial position in which the resiliency of the implant 20 causes the engaging members 28 to withdraw out of the slots 46, thereby releasing the implant 20 from the delivery assembly 12 (FIGS. 7B-C). It will be appreciated that the movement of the inner tubular member 50 between first and second axial positions provides a controlled release in stages of the respective first 32 and second 34 plurality of engaging members. For example, either the first plurality of engaging members 32 may be released from the delivery assembly 12 before the second plurality of engaging members 34 are released, or the first plurality of engaging members 32 may be released from the delivery assembly 12 after the second plurality of engaging members 34 are released.

The medical assembly 10 may further include a flushing port (not shown) that when used in connection with the delivery assembly 12 facilitates flushing capabilities of the medical assembly 10. Additionally, since the implant 20 is positioned over the delivery assembly 12 (i.e. on the outer surface 42 of the outer tubular member 40), and not within the delivery assembly 12 (e.g. within the inner tubular member 50) movement of the guidewire 72 is minimized during deployment of the implant 20. The position of the guidewire 72 is not altered or minimally altered when the implant 20 is released from the delivery assembly 12.

FIG. 8 illustrates another embodiment of the delivery assembly 12, where the inner tubular member 50 includes bellows 59 at a distal portion 53 of the inner tubular member.

Figure 9:
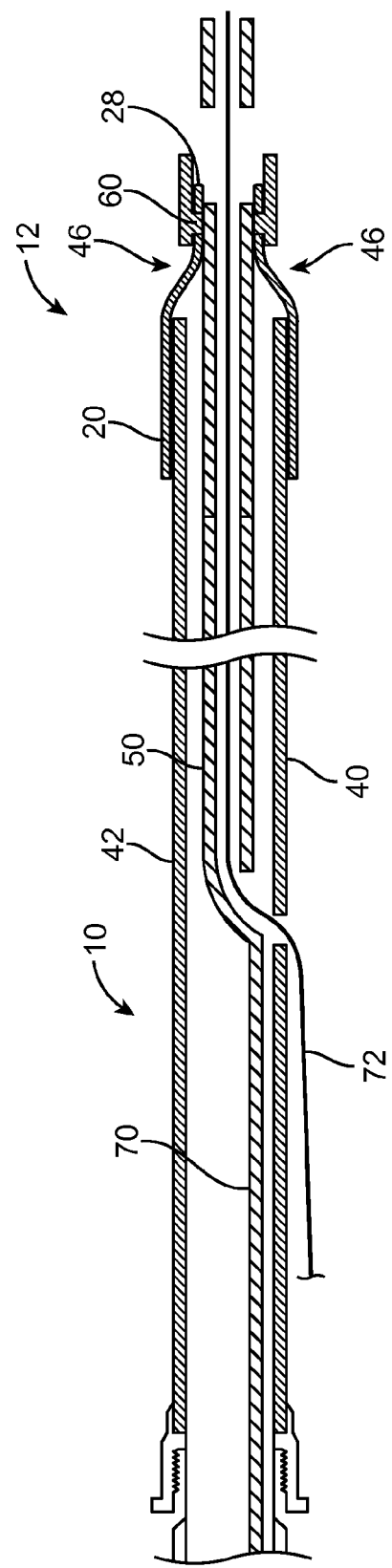
FIG. 9 is cross-sectional views of some embodiments of the disclosed inventions.

FIG. 9 illustrates an alternative embodiment of the medical assembly 10 where the implant 20 includes a plurality of engaging members 28 that extend from either the distal end or the proximal end (not shown) of the implant 20 and are biased to extend radially inward or otherwise elastically deformed into the lumen 26 of the implant 20. The outer tubular member 40 extends through the inner lumen 26 of the implant 20 and has a plurality of slots 46 to receive the engaging members 28 when the implant 20 is on an outer surface 42 of the outer tubular member 40. The inner tubular member 50 is coaxially disposed within the outer tubular member 40 and movable relative to the outer tubular member 40 to release the implant 20 from the delivery assembly 12. The various arrangements and configurations of the engaging members 28 of the implant 20 and delivery assembly interface 12 as shown in FIGS. 5A-6D may be used in the embodiment of FIG. 9, as long as the implant 20 includes engaging members at one of its ends.

What is claimed is:

1. A medical assembly for delivering an implant into a target site of a patient, the assembly comprising:
   a resilient tubular implant having a proximal end, a distal end, and defining an inner lumen extending therebetween, the implant comprising a first plurality of engaging members extending proximally from the proximal end, and a second plurality of engaging members extending distally from the distal end, the implant having a delivery configuration in which the implant is radially constrained, and a released configuration in which the implant is radially expanded, wherein the respective engaging members of the first and second plurality of engaging members are biased to extend radially inward in the released configuration; and
   a delivery assembly for delivering the implant, the delivery assembly comprising
      an outer tubular member extending through the inner lumen of the implant, the outer tubular member having a first plurality of slots receiving therethrough the first plurality of engaging members, and a second plurality of slots receiving therethrough the second plurality of engaging members, respectively, with the implant being disposed in its delivery configuration on an outer surface of the outer tubular member, and
      an inner tubular member coaxially disposed within the outer tubular member and movable relative to the outer tubular member, the inner tubular member having a first axial position in which the inner tubular member restrains the respective first and second pluralities of engaging members between an outer surface of the inner tubular member and an inner surface of the outer tubular member, and a second axial position in which the resiliency of the implant causes the first and second plurality of engaging members to withdraw out of the respective first and second plurality of slots, thereby releasing the implant from the delivery assembly.

2. The medical assembly of claim 1, wherein the engaging members of the first and second pluralities of engaging members have paddle-shaped configurations, each engaging member including a first portion that extends from the implant through a respective slot in the outer tubular member.

3. The medical assembly of claim 2, wherein each engaging member further comprises a second portion that engages a respective protrusion extending radially inward from the inner surface of the outer tubular member or extending radially outward from the outer surface of the inner tubular member.

4. The medical assembly of claim 3, wherein the protrusions extend radially outward from the outer surface of the inner tubular member.

5. The medical assembly of claim 3, wherein the second portion of each engaging member comprises a loop-shaped configuration.

6. The medical assembly of claim 3, wherein the second portion of each engaging member comprises a hook-like configuration or a C-shaped configuration.

7. The medical assembly of claim 3, wherein the protrusions extend radially inward from the inner surface of the outer tubular member.

8. The medical assembly of claim 7, wherein the inner tubular member comprises a first plurality of openings therein and a second plurality of openings therein, wherein the first and second plurality of openings are sized to release the respective first and second plurality of engaging members from the protrusions and out of the respective first and second plurality of slots when the inner tubular member is moved from the first axial position to the second axial position.

9. The medical assembly of claim 1, wherein movement of the inner tubular member from the first axial position to the second axial position provides a controlled release in stages of the respective first and second plurality of engaging members of the implant.

10. The medical assembly of claim 1, the delivery assembly further comprising a detachment member secured to a proximal portion of the inner tubular member for moving the inner tubular member from the first axial position to the second axial position.

11. The medical assembly of claim 1, further comprising a guidewire having a distal end portion slidably disposed within the inner tubular member.

12. A medical assembly for delivering an implant into a target site of a patient, the assembly comprising:
   a resilient tubular implant defining an inner lumen extending therebetween, the implant comprising a plurality of engaging members extending from an end thereof, the implant having a delivery configuration in which the implant is radially constrained, and a released configuration in which the implant is radially expanded, wherein the engaging members are biased to extend radially inward in the released configuration; and
   a delivery assembly for delivering the implant, the delivery assembly comprising
      an outer tubular member extending through the inner lumen of the implant, the outer tubular member having a plurality of slots receiving therethrough the engaging members, with the implant being disposed in its delivery configuration on an outer surface of the outer tubular member, and
      an inner tubular member coaxially disposed within the outer tubular member and movable relative to the outer tubular member, the inner tubular member having a first axial position in which the inner tubular member restrains the engaging members between an outer surface of the inner tubular member and an inner surface of the outer tubular member, and a second axial position in which the resiliency of the implant causes the engaging members to withdraw out of the slots, thereby releasing the implant from the delivery assembly.

13. The medical assembly of claim 12, the delivery assembly further comprising a detachment member secured to a proximal portion of the inner tubular member for moving the inner tubular member from the first axial position to the second axial position.

14. The medical assembly of claim 12, wherein the engaging members have paddle-shaped configurations, each engaging member including a first portion that extends from the implant through a respective slot in the outer tubular member.

15. The medical assembly of claim 14, wherein each engaging member further comprises a second portion that engages a respective protrusion of the delivery assembly.

16. The medical assembly of claim 15, wherein the protrusions extend radially outward from the outer surface of the inner tubular member.

17. The medical assembly of claim 15, wherein the second portion of each engaging member comprises a loop-shaped configuration.

18. The medical assembly of claim 15, wherein the second portion of each engaging member comprises a hook-like configuration or a C-shaped configuration.

19. The medical assembly of claim 15, wherein the protrusions extend radially inward from the inner surface of the outer tubular member.

20. The medical assembly of claim 19, wherein the inner tubular member comprises a plurality of openings sized to release the engaging members from the protrusions and out of the slots when the inner tubular member is moved from the first axial position to the second axial position.

* * * * *